United States Patent [19]

Gough

[11] Patent Number: 4,861,999

[45] Date of Patent: Aug. 29, 1989

[54] SUPERSONIC NOZZLE FOR USE IN AN INFRARED SPECTROMETER

[76] Inventor: Terrance E. Gough, R.R. #5, Cambridge, Ontario, Canada, N1R 5S6

[21] Appl. No.: 87,361

[22] Filed: Aug. 20, 1987

[51] Int. Cl.⁴ .............................................. G01N 21/03
[52] U.S. Cl. ..................................... 250/339; 250/343
[58] Field of Search ................ 250/339, 343, 428, 576; 356/440

[56] References Cited

U.S. PATENT DOCUMENTS

| | | | |
|---|---|---|---|
| 2,731,877 | 1/1956 | Clamann | 356/128 |
| 3,901,820 | 8/1975 | Wood | 250/343 |
| 4,440,013 | 4/1984 | Adams | 73/23.1 |
| 4,717,827 | 1/1988 | Harvey | 250/343 |
| 4,730,111 | 3/1988 | Vestal et al. | 250/288 |

FOREIGN PATENT DOCUMENTS 8801053 2/1988 World Int. Prop. O. .......... 250/343

Primary Examiner—Janice A. Howell
Assistant Examiner—Constantine Hannaher
Attorney, Agent, or Firm—Daryl W. Schnurr

[57] ABSTRACT

This invention relates to a supersonic nozzle (2) for injecting a gas into an infrared spectrometer, said nozzle having an aperture (24) that produces a one-dimensional expansion of said gas. The nozzle has an entrance (4) and exit (6) and between the aperture (24) and the exit (6) is a region for one-dimensional expansion of the gas. The region has two windows (14) that extend on either side of said aperture (24) towards said exit, said windows having an interior surface (30) that is set back slightly from said aperture (24). The windows (14) are made of an appropriate material such as zinc selenide to pass infrared rays and allow the gas to expand in one dimension only.

15 Claims, 4 Drawing Sheets

SUPERSONIC NOZZLE FOR USE IN AN INFRARED SPECTROMETER

BACKGROUND OF THE INVENTION

1. Field of the Invention

This invention relates to a supersonic nozzle for injecting a gas into an infrared spectrometer and, in particular, to a supersonic nozzle having an aperture that produces a one-dimensional expansion of said gas.

2. Description of the Prior Art

It is known to use laser technology to record spectra of gases in jets. In fact, because of the success of laser technology in this area, the use of conventional spectrometers has been almost totally neglected. While nozzles have been used during experimentation in FTIR spectroscopy, the results previously obtainable are much inferior to the resolution and sensitivity of laser techniques. Further, previous nozzles could not be used to produce clusters.

SUMMARY OF THE INVENTION

In accordance with the present invention, a supersonic nozzle, for dispersing a gas in an infrared spectrometer having a pumping system for pumping said gas through said spectrometer, has an entrance and exit for said gas. There are means at said entrance and exit for connecting said nozzle into said spectrometer so that the gas to be analyzed will flow through said nozzle from said entrance to said exit using the pumping system of said spectrometer. A narrow passageway extends from said entrance to a wall containing an aperture. Two windows extend from either side of said aperture towards said exit, each window being normal to a plane formed by said aperture and parallel to the other window. Each window has an interior surface that is set back slightly from said aperture. The windows together define a region for one-dimensional expansion of said gas, said windows being of an appropriate material to pass infrared rays. There are means in said spectrometer to pass infrared rays through said panels. An expansion chamber is located between said windows and said exit, said chamber being substantially larger than said one-dimensional expansion region.

Preferably, the nozzle is a narrow slit having two ends and the windows extend from either end of said slit towards said exit, each window being normal to an imaginary straight line extending between the ends of said slit.

BRIEF DESCRIPTION OF THE DRAWINGS

In drawings which illustrate a preferred embodiment of the invention.

DESCRIPTION OF A PREFERRED EMBODIMENT

Figure 1:
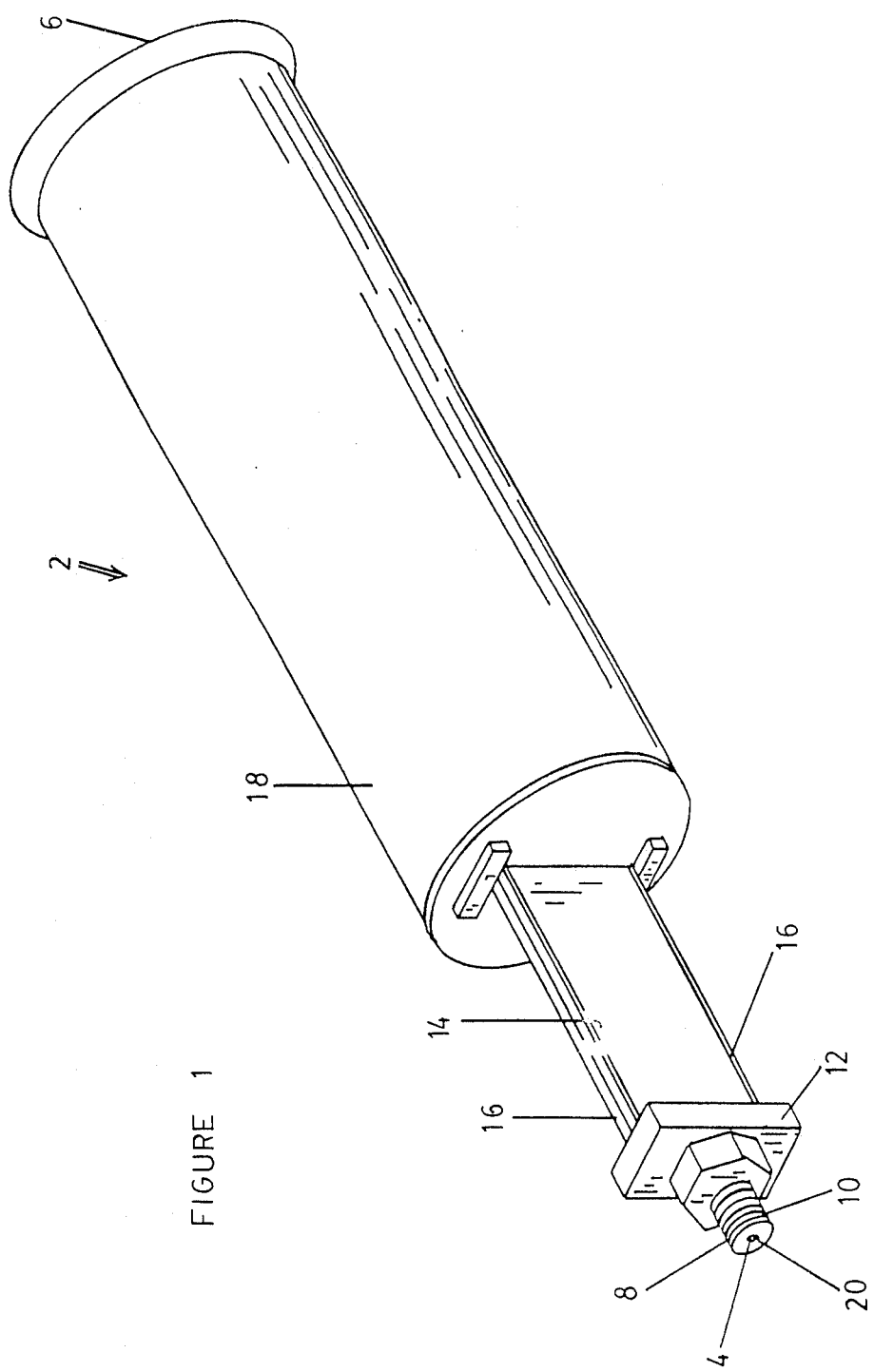
FIG. 1 is a perspective view of one embodiment of a supersonic nozzle.

Referring to the drawings in greater detail, in FIG. 1, a supersonic nozzle 2 for injecting a gas in an infrared spectrometer (not shown), has an entrance 4 and an exit 6. A pumping system (not shown) pumps said gas through said spectrometer. There are means at said entrance 4, being a swagelok fitting 8 for connecting said nozzle 2 into said spectrometer. The swagelok fitting 8 has a threaded portion 10 and a base 12. The base 12 is in turn affixed to two windows 14 (only one of which is shown in FIG. 1). The windows 14 are parallel to one another and together with a top and bottom 16 enclose a one-dimensional expansion region. The bottom 16 is a mirror image of the top 16. Between the windows 14 and the exit 6 is an expansion chamber 18, said chamber being substantially larger than said one-dimensional expansion region. The swagelok fitting 8 has a narrow pasageway 20 centrally located therein. As can best be seen from FIGS. 4 and 5, a rectangular housing 21 extends from the base 12 to a wall 22 containing an aperture 24. The narrow passageway 20 extends from the threaded portion 10 of the swagelok fitting 8, through the base 12 and rectangular housing 21 to the aperture 24 in the wall 22. Windows 14 extend from either side of said aperture 24 and actually commence between the aperture 24 and the base 12. Each window 14 is parallel to a plane formed by said aperture and parallel to the other window 14. Each window 14 has an interior surface 30 that is set back slightly from said aperture 24. The windows 14 together define a one-dimensional expansion region 32 for expansion of the gas being analyzed after it passes through the aperture 24.

Figure 2:
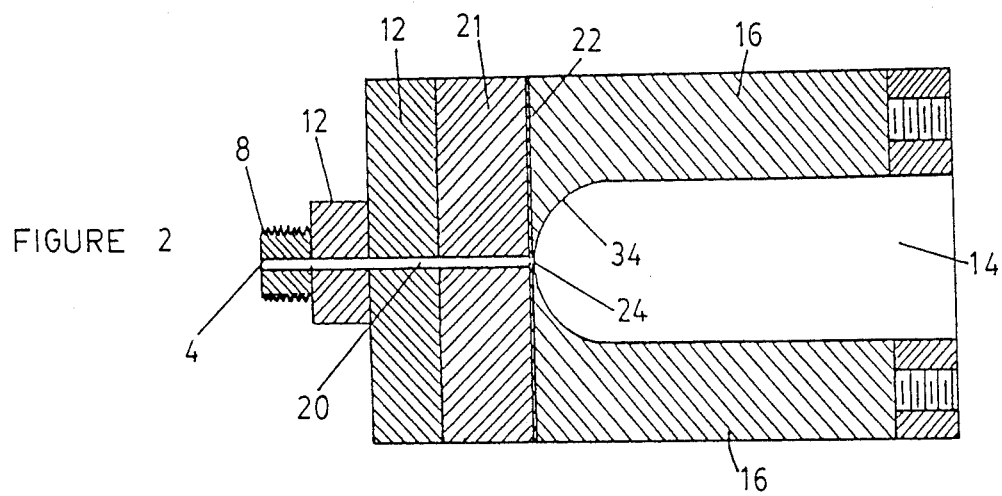
FIG. 2 is a sectional side view of part of the nozzle of FIG. 1.
Figure 3:
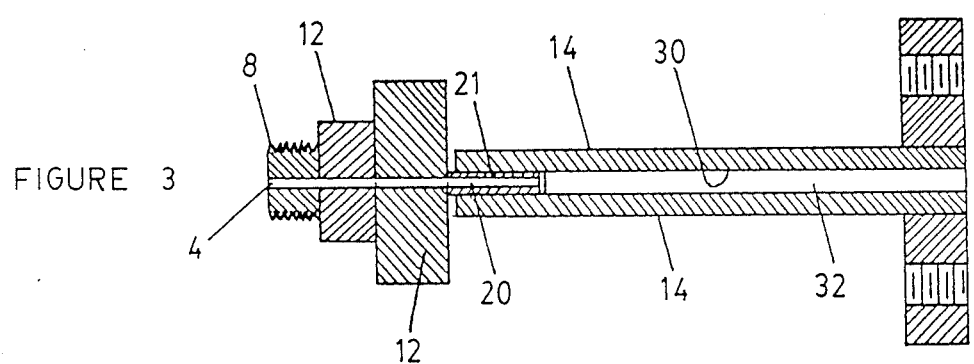
FIG. 3 is a sectional top view of part of the nozzle of FIG. 1.

The top and bottom 16 combine with the windows 14 to completely enclose the region 32. The top and bottom 16 each have an interior surface 34, that tapers toward either side of said slit at an angle of approximately 45° relative to the wall 22 to approximate anticipated stream lines of the expanding gas. Preferably, the tapered portion of the interior surface 34 of said top and bottom 16 on either side of said slit 24 has a semi-circular cross-section as shown in FIG. 2. The windows 14 of FIGS. 2 and 3 are rectangular in shape and extend to the relatively large expansion chamber 18 (not shown in FIGS. 2 and 3) between the windows 14 and the exit 6.

Figure 4:
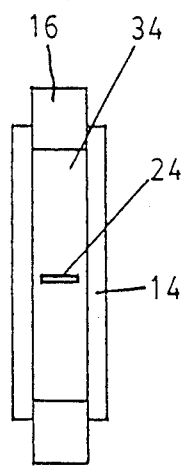
FIG. 4 is an end view of an aperture in the form of a narrow slit.
Figure 5:
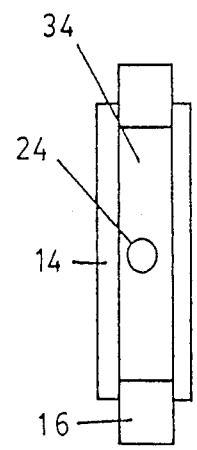
FIG. 5 is an end view of an aperture in the form of a circle.
Figure 6:
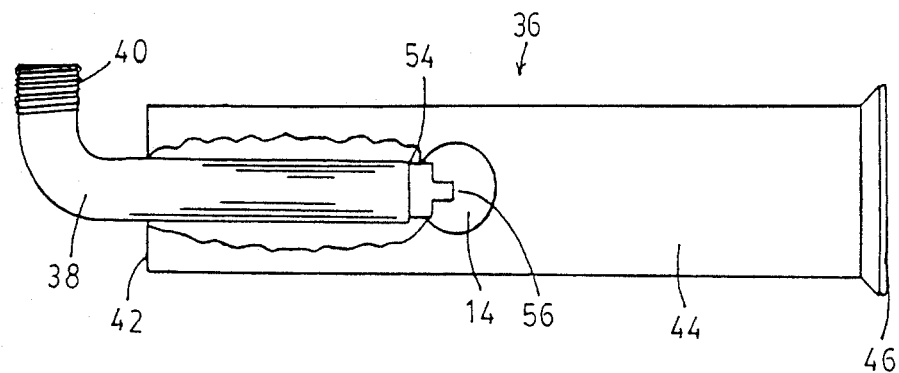
FIG. 6 is a partially cut-away side view of a further embodiment of a supersonic nozzle.
Figure 7:
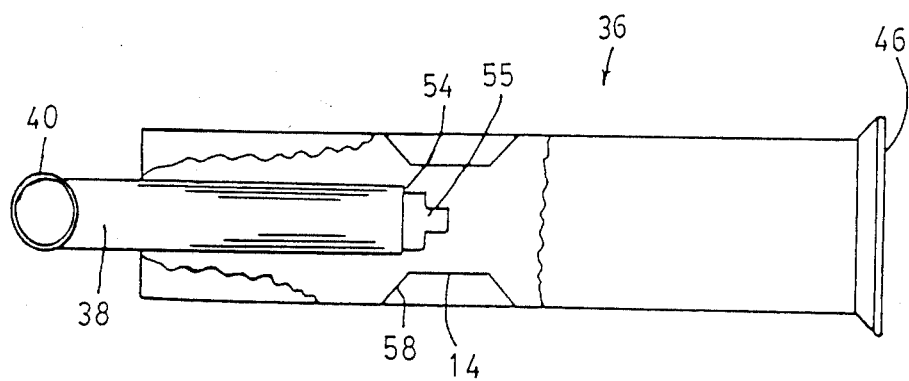
FIG. 7 is a partially cut-away top view of the nozzle of FIG. 6.
Figure 8:
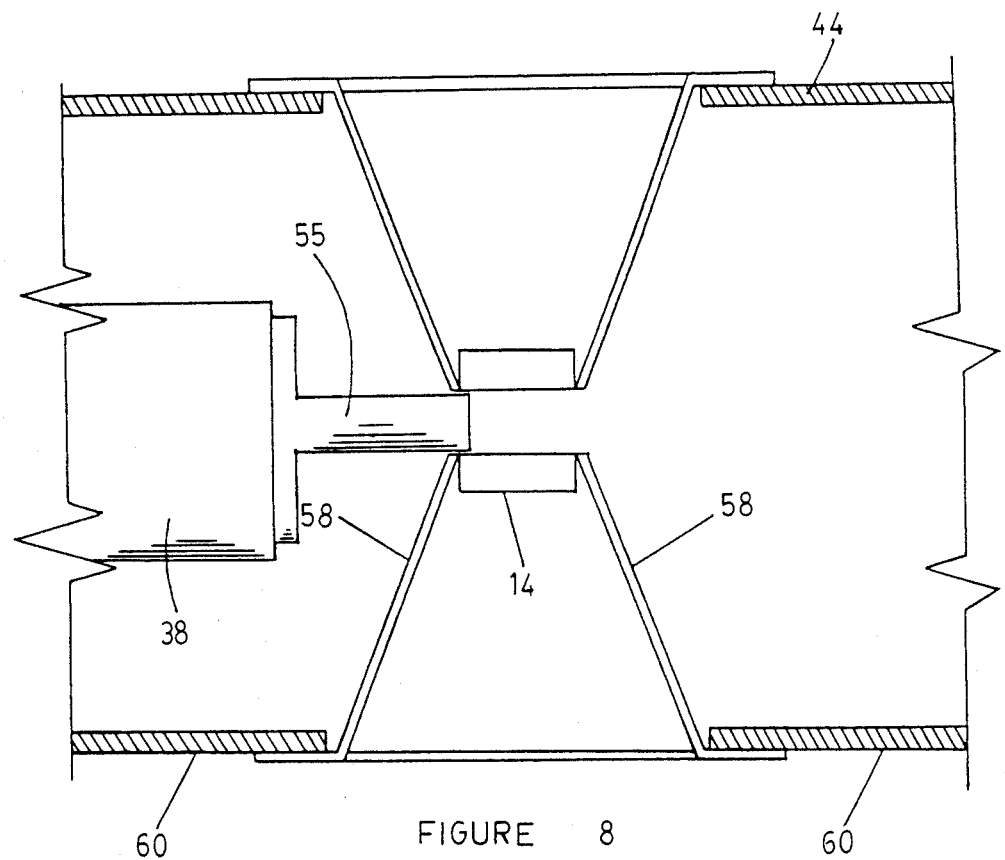
FIG. 8 is an enlarged partial top view of a window assembly in the nozzle of FIG. 6.

As shown in FIG. 4, the aperture 24 in the wall 22 is in the form of a narrow slit. The windows extend from either end of said slit towards said exit, each window being normal to an imaginary straight line extending between the ends of said slit. The slit and nozzle are oriented so that the direction of the spectrometer's radiation beam is parallel to said slit. In FIG. 5, the aperture 24 is in the form of a circle. Both apertures 24 are centrally located between the windows 14, which are set back slightly from the apertures. The distance of setback shown in FIGS. 4 and 5 is exaggerated for ease of illustration.

In a further embodiment of the invention, as shown in FIGS. 6, 7, 8 and 9, the windows 14 can be suspended on either side of said aperture 24. The same reference numerals as those used for the nozzle 2 are used in FIGS. 6 to 9 for those components that are the same or similar. The nozzle 36 has a tube 38 with a threaded entrance 40. The tube 38 extends into one end 42 of a housing 44. The other end 46 of the housing 44 is an exit similar to the exit 6 of the nozzle 2.

The tube 38 extends partially into the housing 44 and terminates at an end 54. In the end 54 is slidably inserted a removable tip 55 which is described in more detail below. While it is not shown in FIGS. 5 to 9, the tip 55 contains an aperture, which is preferably in the form of a slit or circle similar to the apertures shown in FIGS. 4 and 5. As can best be seen from FIG. 8, windows 14 are suspended on either side of the tip 55 and extend towards the exit 46. The windows have a round shape and are preferably made from zinc selenide or any other suitable material that will pass infrared rays. The windows 14 are parallel to one another and normal to an end wall 56 of the tip 55. From either side of the windows 14, support panels 58 are affixed. The support panels 58 have the shape of a truncated cone and extend from the windows 14 to the outer wall 60 of the housing 44 where they are sealed to said outer wall.

Figure 9:
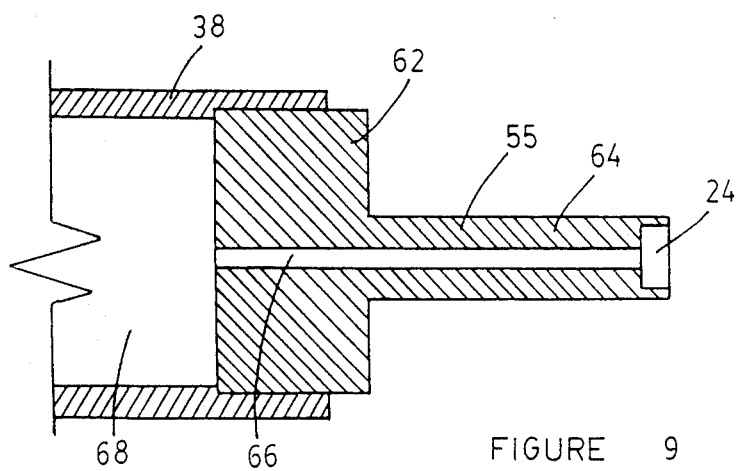
FIG. 9 is an enlarged view of a tip of the nozzle containing an aperture.

The tip 55 is described in more detail in FIG. 9. The tip 55 can be slidably inserted into the tube 38. The tip 55 has a T-shaped cross-section with a base 62 and a projection 64. The projection 64 has an end wall 56 which contains an aperture 24. The aperture 24 is connected by a centrally located passageway 66 to an interior 68 of the tube 38. The advantage of using a nozzle having a tip 55 is that various tips can be designed, each having an aperture of a different size and shape. Depending on the particular type of aperture desired by an operator of the mass spectrometer, the appropriate tip can be inserted into the tube 38. When a different tip is desired, it is a relatively simple matter to remove one tip and replace it with another tip. As an alternative, the tube 38 could have an end wall which contained an aperture of a fixed size and shape.

Examples of some of the sizes that have actually been used successfully with a nozzle similar to that shown in FIGS. 6, 7, 8, 9 are as follows:

Diameter of circular aperture—100 $\mu$m;
Slit aperture—40 $\mu$m $\times$ 750 $\mu$m;
Diameter of end wall containing aperture—1.25 mm;
Thickness of end wall containing aperture—200 $\mu$m;
Distance between zinc selenide windows—2 mm;
Outside diameter of brass tube, being narrow portion of housing—25 mm;
Clear opening provided by windows—5 mm diameter.

Using the narrow slit nozzle of the present invention, cold gas and clusters were observed up to approximately 2 cm from the nozzle. Therefore, it can be concluded that the nozzle is able to produce an extended "zone of silence". Clusters are formed of matter intermediate between infinite solid and monomeric gas. FTIR spectroscopy has well known advantages over laser systems: firstly, the spectral coverage available with FTIR is vastly superior; secondly, the ability to record all transitions in the spectrum at the same time is particularly important for the richer spectra of larger van der Waal's dimers. With the nozzle of the present invention FTIR spectroscopy compares favourably with laser systems. It can be extremely important to produce clusters in a nozzle expansion of a gas. However, up to the time of the present invention, clusters were not able to be produced using supersonic nozzles, in amounts sufficient for detection by FTIR spectroscopy.

I claim:

1. A supersonic nozzle for injecting a gas in an infrared spectrometer using a pumping system for pumping said gas through said spectrometer, said nozzle comprising:
   (a) an entrance and an exit for said gas with means at said entrance and at said exit for connecting said nozzle into said spectrometer so that gas to be analyzed will flow through said nozzle from said entrance to said exit using the pumping system;
   (b) a narrow passageway extending from said entrance to a wall containing an aperture;
   (c) two windows extending from either side of said aperture towards said exit, each window being normal to a plane formed by said aperture and parallel to the other window, each window having an interior surface that is set back slightly from said aperture, said windows together defining a region for one-dimensional expansion of said gas said windows being of an appropriate material to pass infrared rays;
   (d) means in said spectrometer to pass infrared rays through said windows; and
   (e) an expansion chamber located between said windows and said exit, said chamber being substantially larger than said one-dimensional space.

2. A nozzle as claimed in claim 1 wherein the aperture is a circular opening.

3. A nozzle as claimed in claim 1 wherein the aperture is a narrow slit having two ends and the windows extend from either end of said slit towards said exit, each window being normal to an imaginary straight line extending between the ends of said slit.

4. A nozzle as claimed in claim 3 wherein the direction of the spectrometer's radiation beam is parallel to said slit.

5. A nozzle as claimed in claim 4 wherein the windows form two sides of a region for one-dimensional expansion of said gas, said region also having a closed top and bottom, said top and bottom being mirror images of one another, said slit having two sides, said top and bottom each having an interior surface that tapers toward either side of said slit at an angle of approximately 45° relative to said wall to approximate anticipated stream lines of the expanding gas.

6. A nozzle as claimed in claim 5 wherein the tapered portion of the interior surface of said top and bottom on either side of said slit has a semi-circular cross-section.

7. A nozzle as claimed in claim 6 wherein the windows are approximately 2 mm apart from one another.

8. A nozzle as claimed in any one of claims 4, 5 or 6 wherein the slit has a width of approximately 40 $\mu$m.

9. A nozzle as claimed in claim 6 wherein a zone of silence can be observed between said windows approximately 2 cm from said slit.

10. A nozzle as claimed in any one of claims 1, 3 or 5 wherein the windows are rectangular in shape and extend to a relatively large expansion chamber between the windows and the exit.

11. A nozzle as claimed in claim 4 wherein the windows are suspended on either side of said slit.

12. A nozzle as claimed in claim 11 wherein the windows are circular in shape.

13. A nozzle as claimed in any one of claims 1, 2 or 3 wherein the windows are made from zinc selenide.

14. A nozzle as claimed in any one of claim 1, 2 or 3 wherein the windows are made from potassium bromide.

15. A nozzle as claimed in claim 1 wherein the expansion chamber extends from said slit to said exit.

* * * * *